United States Patent
Liang et al.

(10) Patent No.: US 8,440,728 B2
(45) Date of Patent: May 14, 2013

(54) METHOD FOR INCREASING THE YIELD OF A SLURRY BED REACTOR

(75) Inventors: Kuo-Chao Liang, Chiayi County (TW); How-Ming Lee, Taoyuan County (TW); Chin-Ching Tzeng, New Taipei County (TW)

(73) Assignee: Atomic Energy Council—Institute of Nuclear Energy Research, Lungtan, Taoyuan (TW)

( * ) Notice: Subject to any disclaimer, the term of this patent is extended or adjusted under 35 U.S.C. 154(b) by 291 days.

(21) Appl. No.: 13/044,739

(22) Filed: Mar. 10, 2011

(65) Prior Publication Data
US 2012/0232174 A1 Sep. 13, 2012

(51) Int. Cl.
*C07C 27/00* (2006.01)
(52) U.S. Cl.
USPC .......................................................... 518/700
(58) Field of Classification Search ................... 518/700
See application file for complete search history.

(56) References Cited

FOREIGN PATENT DOCUMENTS
WO WO8500875 A1 2/1985

OTHER PUBLICATIONS

Alpay et al (conference proceedings, Hungarian Journal of Industrial chemistry (1999), 1 (1, novel chemical reaction engineering for cleaner technologies), 1-8.*
Gallucci et al, "A Theoretical Analysis of Methanol Synthesis from CO2 and H2 in a Ceramic Membrane Reactor", Int. Journal of Hydrogen Energy, 32, Dec. 2007, pp. 5050-5028.

* cited by examiner

*Primary Examiner* — Jafar Parsa
(74) *Attorney, Agent, or Firm* — Jackson IPG PLLC

(57) ABSTRACT

Disclosed is a method for increasing the yield of a slurry bed reactor. The method provides a slurry bed reactor with a recycling unit or a replacing unit. An absorbing agent is fed into the slurry bed reactor. The absorbing agent is a substance that can react with at least one product of a primary reaction or at least one reactant of a side reaction. Then, the absorbing agent is transmitted into the recycling unit or the replacing unit. The recycling unit renews the absorbing agent and sends the renewed absorbing agent back into the slurry bed reactor for reuse. The replacing unit replaces the absorbing agent with new absorbing agent and sends the new absorbing agent into the slurry bed reactor for use.

10 Claims, 3 Drawing Sheets

METHOD FOR INCREASING THE YIELD OF A SLURRY BED REACTOR

BACKGROUND OF THE PRESENT DISCLOSURE

1. Technical Field

The present disclosure relates to a method for increasing the yield of a slurry bed reactor and, more particularly, to a method for increasing the yield of a slurry bed reactor by using absorbing agent to remove at least one product of a primary reaction or at least one reactant of a side reaction.

2. Related Prior Art

A slurry bed reactor is suitable for an exothermal reaction for making methanol or dimethyl ether for example because it uses solvent with high heat capacity and excellent heat transfer and involves a simple structure. About 5000 million tons of methanol were produced around the world in the year of 2009. The production of methanol is of a considerable commercial value.

Generally, if a chemical reaction is a reversible reaction, the chemical reaction will eventually reach thermodynamic equilibrium where the equilibrium conversion ratio of the chemical reaction is the highest. In the industry, because the reactants cannot be used completely, some of the reactants must be separated from the products and reused. The lower the equilibrium conversion ratio is, the more of the reactants have to be recycled, and the higher the cost. If some of the products can be removed, the chemical equilibrium is moved toward the products and the conversion ratio of the reactants is increased. For example, the chemical reaction of carbon oxide (CO) with nitrogen oxide (NO2) to produce carbon dioxide (CO2) and nitrogen oxide (NO) is a reversible reaction. The chemical reaction is represented by a formula as follows:

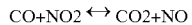

CO+NO2 ↔ CO2+NO

The equilibrium constant Keq=[CO2]eq[NO]eq/[CO]eq[NO2]eq. If the carbon dioxide is removed after the chemical reaction, the chemical reaction will be moved to the right, thus facilitating further production of the carbon dioxide from the carbon oxide and increasing the use of the reactants.

Sometimes, in a reactor, there are several chemical reactions represented by the formulae as follows:

$$A+B=C+D \quad (1)$$

$$A+D=E+F \quad (2)$$

wherein C is the primary product, if some of D is removed during the chemical reactions, the side products of equation (2) will be reduced and the primary product C will be increased.

Examples of chemical reactions based on the foregoing principle can be found in some documents. In Gallucci and Basile, Int. J. Hydrogen Energy, 32, 5050, 2007 for example, a fixed bed reactor is used to produce methanol from carbon dioxide and hydrogen (CO2+H2 ↔ CH3OH+H2O), and a film can be used to remove the methanol or water to increase the conversion ratio. However, no document has proposed removing at least one product from a chemical reaction executed in a slurry bed reactor to increase the conversion ratio of at least one reactant.

The present disclosure is therefore intended to obviate or at least alleviate the problems encountered in prior art.

SUMMARY OF THE PRESENT DISCLOSURE

It is the primary objective of the present disclosure to provide a method for increasing the yield of a slurry bed reactor by using absorbing agent to remove at least one product of a primary reaction or at least one reactant of a side reaction.

To achieve the foregoing objective, the method includes the step of providing a slurry bed reactor with a recycling unit or a replacing unit. An absorbing agent is fed into the slurry bed reactor. The absorbing agent is a substance that can react with at least one product of a primary reaction or at least one reactant of a side reaction. Then, the absorbing agent is transmitted into the recycling unit or the replacing unit. The recycling unit renews the absorbing agent and sends the renewed absorbing agent back into the slurry bed reactor for reuse. The replacing unit replaces the absorbing agent with new absorbing agent and sends the new absorbing agent into the slurry bed reactor for use.

In an aspect, the absorbing agent is liquid or solid.

In another aspect, the recycling unit is located inside or outside the slurry bed reactor.

In another aspect, the replacing unit is located inside or outside the slurry bed reactor.

Other objectives, advantages and features of the present disclosure will be apparent from the following description referring to the attached drawings.

BRIEF DESCRIPTION OF THE DRAWINGS

The present disclosure will be described via detailed illustration of two embodiments referring to the drawings wherein.

DETAILED DESCRIPTION OF THE EMBODIMENTS

Figure 1:
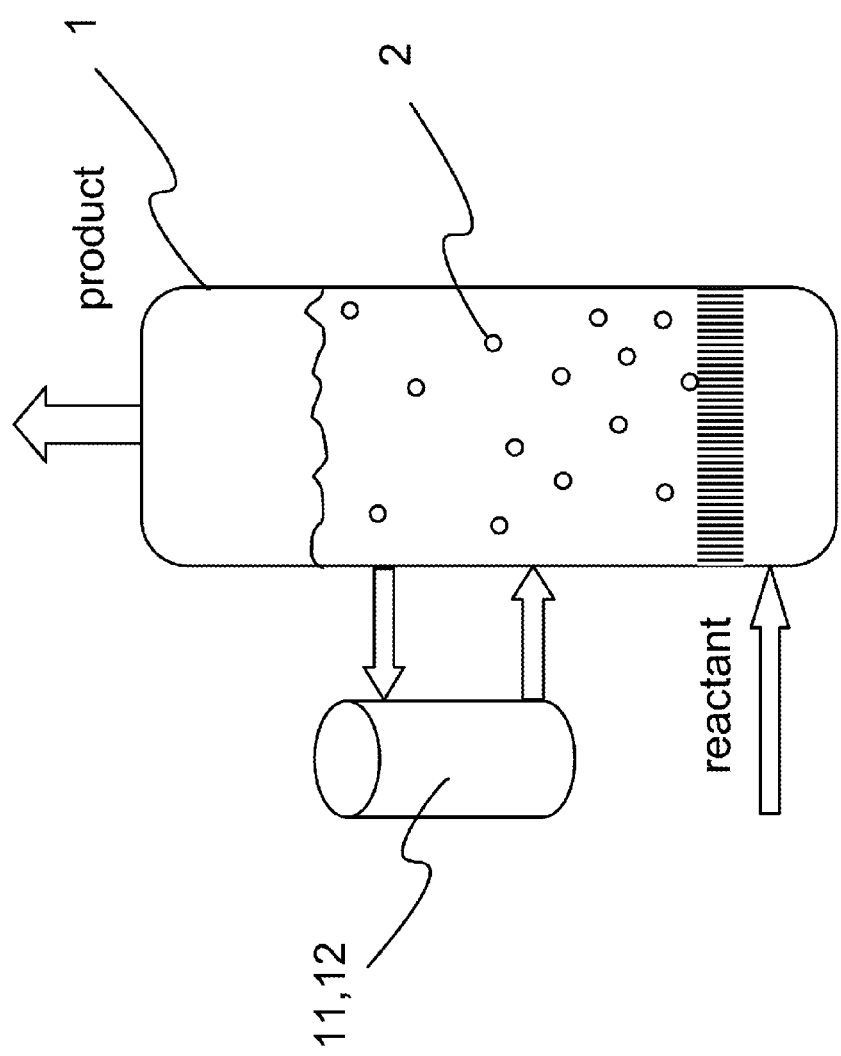
FIG. 1 is a block diagram of a slurry bed reactor in which a method is used for increasing the yield according to the first and second embodiments of the present disclosure.

FIG. 1 shows a slurry bed reactor 1 in which a method is used for increasing the yield according to the present disclosure. The slurry bed reactor 1 includes a recycling unit 11 or a replacing unit 12. The recycling unit 11 or the replacing unit 12 can be located inside or outside the slurry bed reactor 1

An absorbing agent 2 is fed into the slurry bed reactor 1. The absorbing agent 2 is a substance that can react with at least one product of a primary reaction or at least one reactant of a side reaction. The absorbing agent 2 can be liquid or solid.

After reacting with the product, the absorbing agent 2 is transmitted into the recycling unit 11. In the recycling unit 11, the absorbing agent 2 is recycled. Thus, the absorbing ability of the absorbing agent 2 is retained in the slurry bed reactor 1.

Alternatively, after reacting with the product, the absorbing agent 2 can be transmitted into the replacing unit 12. The absorbing agent 2 is removed from the replacing unit 12 while new absorbing agent 2 is fed into the slurry bed reactor 1 through the replacing unit 12. Thus, the absorbing ability of the absorbing agent 2 is retained in the slurry bed reactor 1.

In operation, in addition to solvent and catalyst, the absorbing agent 2 is fed into the slurry bed reactor 1 to react with at least one product of the primary reaction to reduce the concentration of the product in the slurry bed reactor 1 so that the primary reaction is moved toward the product according to Le Chatelier's principle to increase the conversion ratio of at least one reactant. Alternatively, the absorbing agent 2 reacts with at least one reactant of the side reaction to reduce the side reaction but increase the production of the product.

After reacting with the product, the absorbing agent 2 is transmitted into the recycling unit 11. In the recycling unit 11, the absorbing agent 2 is renewed and fed back into the slurry bed reactor 1.

Alternatively, after reacting with the product, the absorbing agent 2 can be transmitted into the replacing unit 12. The absorbing agent 2 is removed from the replacing unit 12 while new absorbing agent 2 is fed into the slurry bed reactor 1 through the replacing unit 12.

Figure 2:
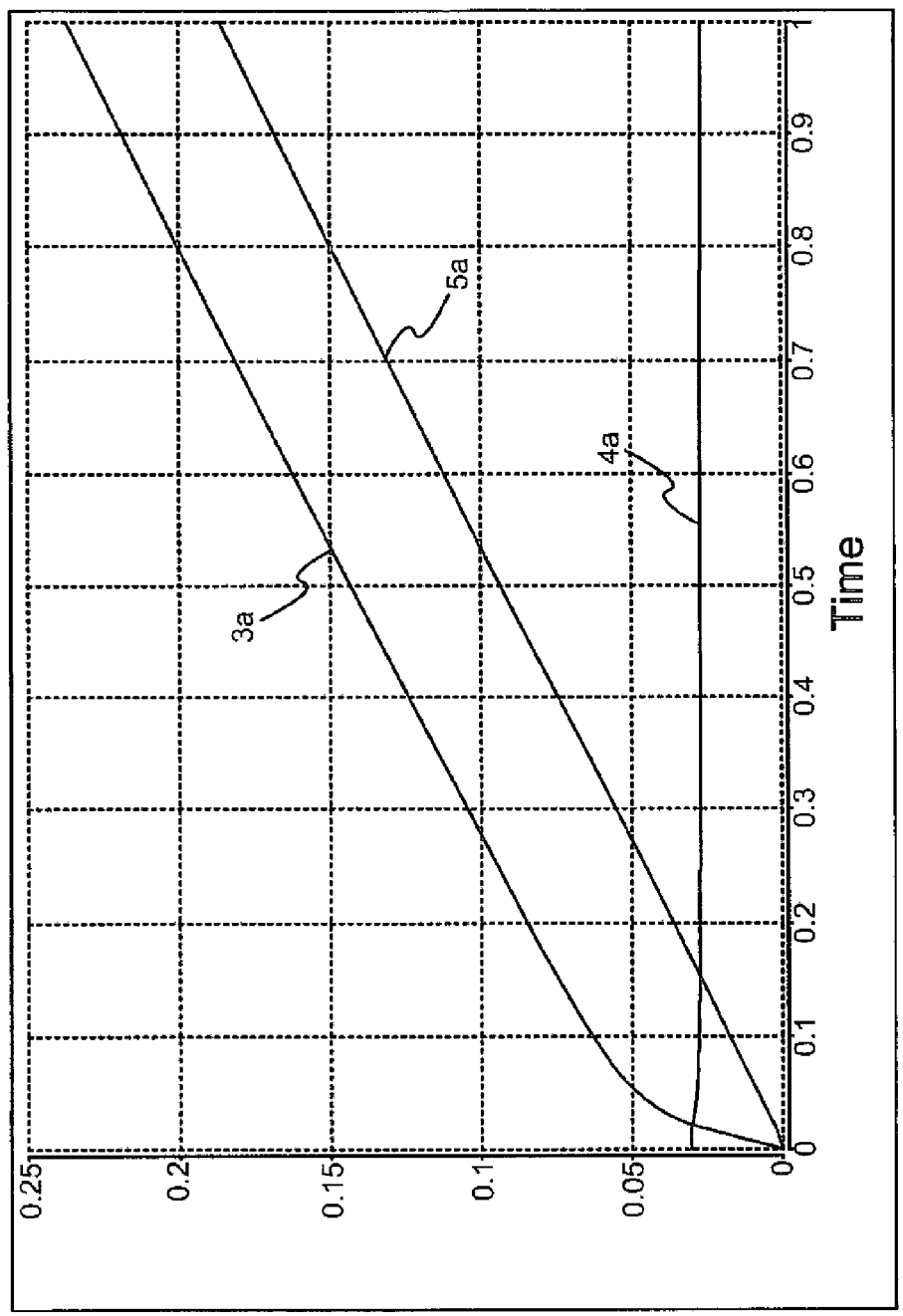
FIG. 2 is a chart of the yield of dimethyl ether in the slurry bed reactor shown in FIG. 1, without any water removed from the slurry bed reactor.
Figure 3:
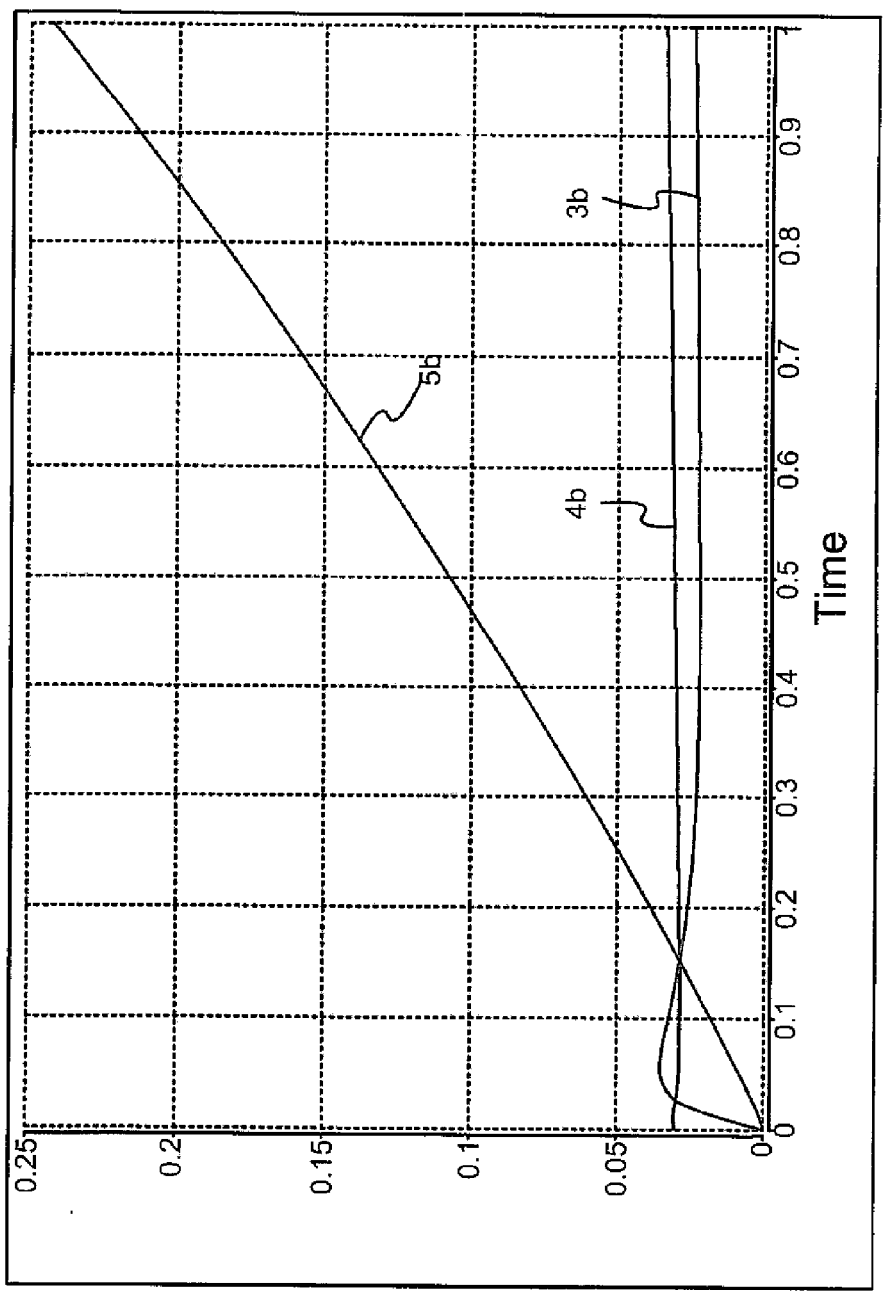
FIG. 3 is another chart of the yield of dimethyl ether in the slurry bed reactor shown in FIG. 1, with water removed from the slurry bed reactor.

FIGS. 2 and 3 in the first embodiment of the present disclosure show water, the absorbing agent 2, is used to remove at least one product of the primary reaction. In the slurry bed reactor 1 for making dimethyl ether from syngas ($CO/CO_2/H_2$), there are chemical reactions represented by the formulae as follows:

$$CO + 2H_2 \leftrightarrow CH_3OH; \quad (1)$$

$$2CH_3OH \leftrightarrow CH_3OCH_3 + H_2O; \quad (2)$$

$$CO + H_2O \leftrightarrow CO_2H_2; \quad (3)$$

wherein the dimethyl ether is the primary product. The absorbing agent 2 is used to absorb some of the water. After some of the water is absorbed by the absorbing agent 2, the production of the dimethyl ether in Formula (2) is increased. Alternatively, some of the carbon dioxide in Formula (3) can be removed to increase the production of the dimethyl ether.

As shown in FIGS. 2 and 3, a one-dimensional cylindrical stream is used to simulate the syngas $CO/CO_2/H_2/N_2=29/3/62/4$. Where the water is not removed from the products, the concentrations of the water, carbon dioxide and dimethyl ether are respectively represented by curves 3a, 4a and 5a in FIG. 2. Where some of the water is removed from the products, the concentrations of the water, carbon dioxide and dimethyl ether are respectively represented by curves 3b, 4b and 5b in FIG. 3. It can be found that removing the water is helpful for increasing the concentration of the dimethyl ether. The absorbing agent 2 is the $KNO_3/LiNO_2$ disclosed in WO 85/00875. Water can be removed from the absorbing agent 2 by the recycling unit 11 so that the absorbing agent 2 can be reused. Alternatively, the absorbing agent 2 can be replaced with new absorbing agent 2 by the replacing unit 12.

According to a second embodiment of the present disclosure, the absorbing agent 2 is used to remove at least one reactant of the side reaction. In the chemical reaction of carbon dioxide with hydrogen to produce methanol in a slurry bed reactor, the chemical reaction is represented by the formula as follows:

$$CO_2 + 3H_2 \leftrightarrow CH_3OH + H_2O;$$

After adding the absorbing agent 2 such as zeolite, water is cured in the absorbing agent 2 to remove water from the slurry bed reactor 1 to increase the conversion ratio of the carbon dioxide to increase the choice ratio of the methanol. After absorbing the water, the zeolite is transmitted into the recycling unit 11 located outside the slurry bed reactor 1 so that the zeolite is renewed and reused. Alternatively, after absorbing the water, the zeolite can be transmitted into the replacing unit 12 located outside the slurry bed reactor 1 so that the zeolite is replaced with new zeolite.

As discussed above, the present disclosure provides a method for increasing the yield of a slurry bed reactor while overcoming the problems encountered in the prior art. The absorbing agent 2 is used in the slurry bed reactor to remove at least one product of the primary reaction or at least one reactant of the side reaction to increase the conversion ratio of the reactant and the choice ratio of the primary product in a reversible reaction to increase the yield of the slurry bed reactor.

The present disclosure has been described via the detailed illustration of the embodiments. Those skilled in the art can derive variations from the embodiments without departing from the scope of the present disclosure. Therefore, the embodiments shall not limit the scope of the present disclosure defined in the claims.

What is claimed is:

1. A method for increasing the yield of a slurry bed reactor, the method comprising:
   providing the slurry bed reactor with an absorbing agent replacing unit;
   feeding an absorbing agent into the slurry bed reactor, the absorbing agent being a substance that reacts with at least one reactant of a side reaction; and
   transmitting the absorbing agent into the replacing unit which replaces the absorbing agent with new absorbing agent and sends the new absorbing agent into the slurry bed reactor for use such that the side reaction is reduced and such that production of at least one product of a primary reaction is increased.

2. The method according to claim 1, wherein the absorbing agent is liquid.

3. The method according to claim 1, wherein the absorbing agent is solid.

4. The method according to claim 1, wherein the replacing unit is located inside the slurry bed reactor.

5. The method according to claim 1, wherein the replacing unit is located outside the slurry bed reactor.

6. A method for increasing the yield of a slurry bed reactor, the method comprising:
   providing the slurry bed reactor with an absorbing agent recycling unit;
   feeding an absorbing agent into the slurry bed reactor, the absorbing agent being a substance that reacts with at least one reactant of a side reaction; and
   transmitting the absorbing agent into the recycling unit which renews the absorbing agent and sends renewed absorbing agent back into the slurry bed reactor for reuse such that the side reaction is reduced and such that production of at least one product of a primary reaction is increased.

7. The method according to claim 6, wherein the absorbing agent is liquid.

8. The method according to claim 6, wherein the absorbing agent is solid.

9. The method according to claim 6, wherein the recycling unit is located inside the slurry bed reactor.

10. The method according to claim 6, wherein the recycling unit is located outside the slurry bed reactor.

* * * * *